United States Patent [19]
Evans

[11] Patent Number: 5,916,229
[45] Date of Patent: Jun. 29, 1999

[54] ROTATING NEEDLE BIOPSY DEVICE AND METHOD

[76] Inventor: Donald Evans, 1405 Huntington Cir., Reno, Nev. 89509

[21] Appl. No.: 08/597,918

[22] Filed: Feb. 7, 1996

[51] Int. Cl.⁶ .................................................. A61B 17/32
[52] U.S. Cl. .......................... 606/171; 606/167; 606/170; 606/180; 604/22; 604/164; 600/652; 600/567; 600/564; 600/568
[58] Field of Search .................... 606/171, 167, 606/170, 180, 174, 162; 604/22, 164; 128/751, 752, 753, 754, 755, 749; 600/562, 567, 564, 568

[56] References Cited

U.S. PATENT DOCUMENTS

| | | | |
|---|---|---|---|
| 3,606,878 | 9/1971 | Kellogg | 606/171 |
| 4,203,444 | 5/1980 | Bonnell et al. . | |
| 4,577,629 | 3/1986 | Martinez | 606/171 |
| 4,589,414 | 5/1986 | Yoshida et al. | 606/171 |
| 4,603,694 | 8/1986 | Wheeler | 606/171 |
| 4,850,354 | 7/1989 | McGurk-Burleson et al. | 128/305 |
| 5,106,364 | 4/1992 | Hayafuji et al. | 606/171 |
| 5,189,751 | 3/1993 | Giuliani et al. . | |
| 5,197,484 | 3/1993 | Kornberg et al. . | |
| 5,395,313 | 3/1995 | Naves et al. . | |
| 5,423,844 | 6/1995 | Miller . | |
| 5,643,304 | 7/1997 | Schechter et al. | 606/171 |
| 5,665,101 | 9/1997 | Becker et al. | 606/180 |
| 5,669,923 | 9/1997 | Gordon | 606/170 |
| 5,720,760 | 2/1998 | Becker et al. | 606/180 |
| 5,722,985 | 3/1998 | Pettus | 606/180 |
| 5,730,752 | 3/1998 | Alden et al. | 606/180 |
| 5,782,764 | 7/1998 | Werne | 606/411 |

*Primary Examiner*—Mickey Yu
*Assistant Examiner*—Dinh X. Nguyen
*Attorney, Agent, or Firm*—Ian F. Burns

[57] ABSTRACT

A biopsy device and method are provided for removing samples of tissue from a patient's body. The device comprises a hollow outer needle with an opening, a rotatable inner needle with a cutting surface and a driving mechanism within a handle assembly. The needles are inserted into the patient's body and the inner needle is rotated so as to expose the cutting surface. The driving mechanism is activated and the inner needle is oscillated along its longitudinal axis at a desired frequency. The inner needle is then rotated and tissue is pinched between the cutting surface and the outer needle. The combination of the pinching force and the oscillating motion severs a uniform sample of tissue. The tissue is captured between the cutting surface of the inner needle and the inner surface of the outer needle. The driving mechanism is then deactivated and the device is removed from the patient's body. The needle portion of the device may be removed from the handle assembly and discarded.

14 Claims, 3 Drawing Sheets

ROTATING NEEDLE BIOPSY DEVICE AND METHOD

BACKGROUND OF THE INVENTION

1. Field of Invention

This invention relates to the removal of living tissues or cells from a body for histological or cytological examination and more particularly to an improved method and apparatus for performing the same.

2. Description of the Related Art

In the United States, cancer is the second most common cause of death, accounting for about one fifth of the total. It has been found that early diagnosis is an important factor in successful treatment of the disease. There are a number of methods for examining suspicious tumors such as X-ray photography, ultrasound imaging and chemical analysis of bodily fluids. However, microscopic examination of the suspect tissue is the most accurate and efficient means of determining malignancy for most tumors.

Microscopic examination for the diagnosis of cancer and other diseases requires that a sample of suspected tissues be removed from the body. When a tumor is close to the surface of the body, this may be done by excising a small portion with a knife or scalpel. However, the excising procedure is not suitable for tumors that are beneath the surface of the body. These tumors are difficult to access and may require general anesthesia to be administered to the patient. Furthermore, the excision procedure usually produces significant trauma to the surrounding tissue and may result in a visible scar which would be undesirable on some portions of the body.

To provide an alternative to the excision procedure, a number of alternative techniques and devices have been developed for performing biopsies. One of these is a needle biopsy which uses a hollow needle and a syringe. The needle is inserted into the body so that the tip is placed inside the target tissue. The plunger of the syringe is then withdrawn to create low pressure. When the device works as intended, tissue is drawn into the needle and the device may then be withdrawn from the body.

One of the disadvantages of the needle biopsy is that it causes trauma to the body tissue and discomfort to the patient. As the plunger of the syringe is withdrawn, tissue is torn from its position in the body and sucked into the needle. The negative pressure created by withdrawing the syringe does not cleanly sever the sample tissue from the surrounding tissue and no cutting surface is provided for severing the tissue. More tissue is torn when the needle is withdrawn from the body. This tearing causes trauma to the surrounding tissue which usually causes pain to the patient during and after the procedure. Even if a local anesthetic is administered to the patient, the trauma may cause some amount of discomfort to the patient during the procedure and a significant amount of discomfort when the anesthetic has worn off.

Another disadvantage of the needle biopsy is that it does not always produce an adequate sample of the target tissue. As the needle is inserted into the body, some amount of non-target tissue is cut from the body along the path of the needle and lodged in the needle's tip. Furthermore, as the plunger of the syringe is withdrawn, some amount of non-target tissue may be drawn into the needle. This unwanted non-target tissue may effect the results of the tissue analysis.

Other needle biopsy devices utilize a design having a needle within a needle. Both needles are inserted into the body and the tip of the outer needle is usually inserted farther into the body than the inner needle thereby creating an internal cavity where tissue is intended to be captured. The outer needle is sometimes driven past the inner needle with the use of a spring activated mechanism. Devices that use spring activated mechanisms are sometimes called punch biopsy devices. When the device works as intended, the needles are withdrawn after the spring mechanism is activated and target tissue is torn from the body.

However, double needle devices and spring activated mechanisms inflict a significant amount of trauma to the patient. This trauma is especially undesirable for elderly patients and patients with hemophilia. In addition, double needle and spring activated biopsy devices produce poor samples. The samples tend to be non-uniform and jagged because of the traumatic way in which samples are retrieved and these samples may fail to retrieve an adequate sample of the target tissue.

SUMMARY OF THE INVENTION

1. Brief Description of the Invention

The present invention comprises a needle assembly and a handle assembly. During normal operation, the two assemblies are secured together to form a single unit. The needle assembly is designed to be inexpensive enough that it may be discarded after one use. The needle assembly includes a hollow outer needle with an opening near the tip of the needle. The opening is oblong shaped and allows tissue to protrude into the interior of the needle. A narrower inner needle is provided within the outer needle. The inner needle is provided with a cutting surface that corresponds to the opening of the outer needle. The cutting surface of the inner needle and the edge of the opening of the outer needle are very sharp and may easily severe tissue when manipulated in the correct manner.

The handle assembly provides a driving mechanism for oscillating one or both of the needles along their longitudinal axis at a high frequency. The driving mechanism may be any of a number of mechanisms that are well known in the art. In the preferred embodiment of the invention, the driving assembly comprises an electromagnet that is similar to a mechanism disclosed in U.S. Pat. No. 5,189,751 to Giuiani et al. Other embodiments may utilize a mechanical linkage to an electrical motor or a solenoid with an oscillating current.

In the preferred embodiment, the inner needle is driven while the outer needle is stationary. A horseshoe-shaped electromagnet interacts with two permanent magnets which are attached to the proximal end of the inner needle. With the polarity of the electromagnet in one orientation, the permanent magnets draw in one direction and the inner needle moves some distance in this direction. When the polarity of the electromagnet is reversed, the permanent magnets are drawn in the opposite direction and the inner needle moves a distance in the opposite direction. By oscillating the polarity of the electromagnet at a desired frequency, a superior cutting action is achieved.

The handle assembly further comprises a power source such as a battery or power cord. The housing of the handle assembly is hermetically sealed so as to prevent contamination of the driving mechanism. The surface of the housing is smooth so as to be easy to clean and provides little surface upon which bacteria may grow.

In the preferred embodiment, the outer needle remains in a fixed position relative to the handle when the needle assembly is secured to the handle assembly. However, the inner needle is driven by the driving mechanism and the inner needle may be pivoted around its longitudinal axis to achieve a cutting action. A collar is provided for the operator to control the rotation of the needle.

The inner needle has a semicircular cross section at its cutting surface. When the inner needle is in one angular position, the opening of the outer needle is aligned with a rounded surface of the inner needle. This is defined as the closed position of the device and the device is placed in this position when the device is inserted into a body. In the closed position, the outer needle and the rounded surface of the inner needle define a relatively smooth surface so that little or no non-target material is disturbed or collected by the needle.

Once inserted into a body and properly located, the inner needle is rotated along its longitudinal axis and the cutting surface becomes exposed to target tissue. The cutting surface and the outer needle define a cavity into which target tissue may protrude. When the inner needle is nearly 180 degrees from its closed position, the cutting surface is almost completely exposed to the target tissue. At this point the driving mechanism of the device is activated and the inner needle begins to vibrate along its longitudinal axis at a desired frequency. The rotation of the inner needle is then reversed. As the inner needle begins to rotate towards its closed position, target tissue is pinched between the cutting surface of the inner needle and the cutting edge of the outer needle. The combination of the pinching action and the vibration of the inner needle result in severing a sample of the target tissue.

2. The Object of the Invention

It is an object of the present invention to provide a biopsy method and device that reduces trauma to the patient.

It is a further object of the present invention to provide a biopsy method and device that reduces discomfort and pain experienced by the patient during and after the biopsy procedure.

It is a further object of the present invention to provide a biopsy method and device that removes less non-target tissue.

It is a further object of the present invention to provide method and device that more efficiently and inexpensively performs biopsies.

It is a further object of the present invention to provide method and device that obtains more uniform samples of target tissue.

These and other objects and advantages of the present invention may be realized by reference to the remaining portion of the specification and drawings.

Figure 1:
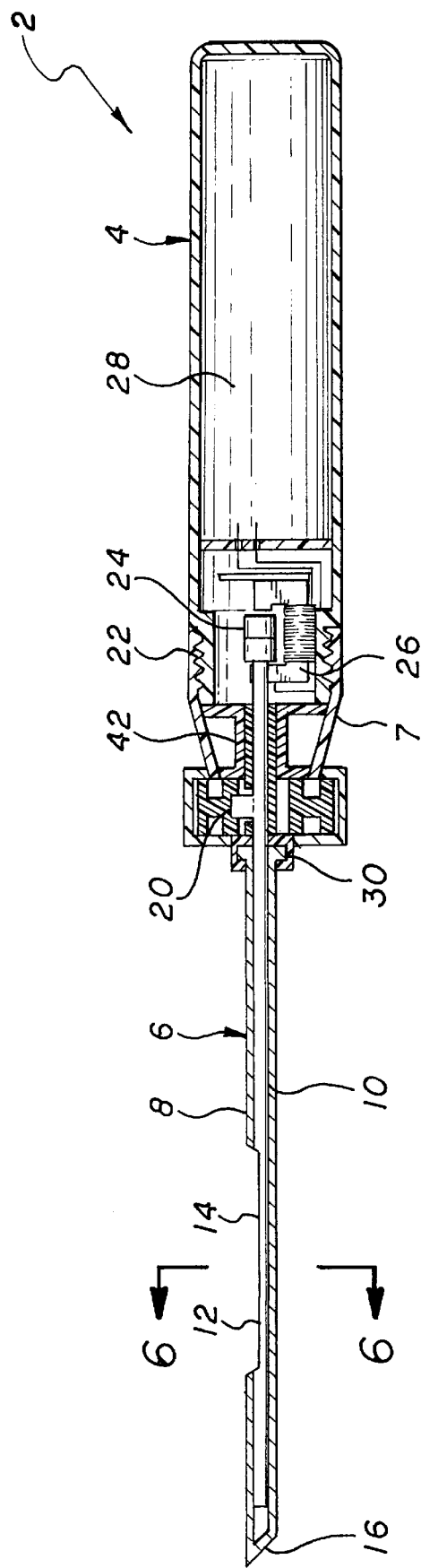
FIG. 1 is a cross-sectional view of one embodiment of the device of the invention.

REFERENCE NUMBERS 2 biopsy device
4 handle assembly
6 needle assembly
7 needle assembly housing
8 outer needle
10 inner needle
12 outer needle opening
13 cutting edge
14 cutting surface
16 outer needle tip
18 rotation mechanism
20 inner needle tab
22 threads
24 permanent magnets
26 electromagnet
27 coil
28 handle cavity
30 outer needle flange
32 electromagnet left end
34 electromagnet right end
36 left permanent magnet
38 right permanent magnet
40 groove
42 guide spacer

DESCRIPTION OF THE PREFERRED EMBODIMENT

Figure 2:
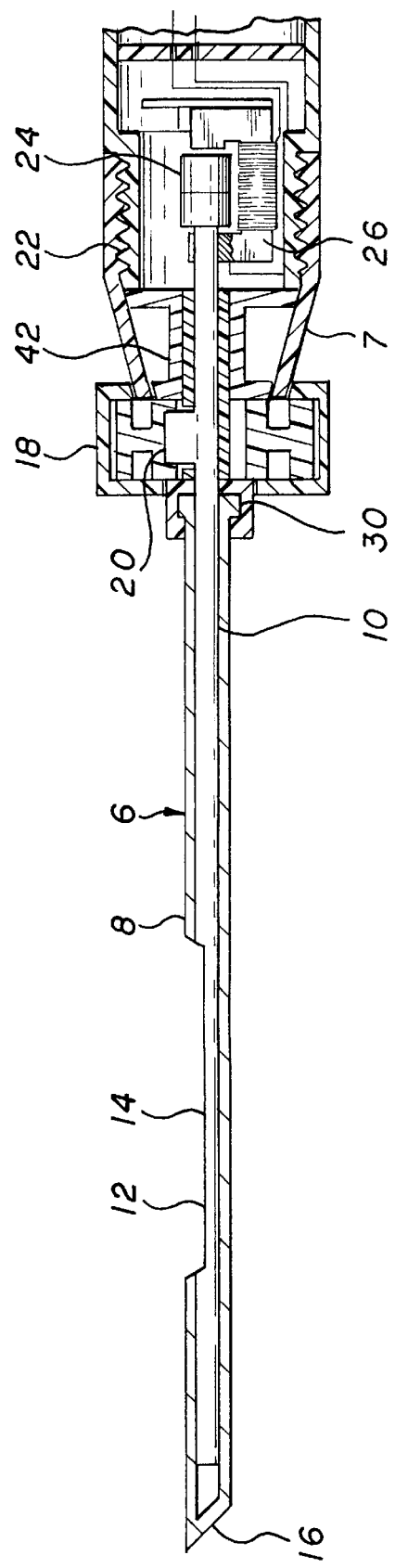
FIG. 2 is an enlarged view of the needle assembly of one embodiment of the invention.

As seen in FIGS. 1 and 2, the present invention comprises a biopsy device 2. Biopsy device 2 comprises a needle assembly 6 and a handle assembly 4. Handle assembly 4 includes means for driving needle assembly 6 and needle assembly 6 includes means for retrieving a tissue sample from within a body. Threads 22 are provided for allowing handle assembly 4 and needle assembly 6 to be easily secured together and separated after use. Needle assembly 4 is intended to be inexpensive to produce so that one can be used for each patient and may be discarded after only one use.

Two needles are provided in needle assembly 6; an outer needle 8 and an inner needle 10. Outer needle 8 is hollow and inner needle 10 is located within outer needle 8. In the preferred embodiment, inner needle 10 may freely rotate within outer needle 8. Outer needle 8 has a beveled tip 16 for aiding the insertion of the device into the body. Tip 16 is closed so that no unwanted tissue will be severed and lodged in outer needle 8. Outer needle 8 also has flange 30 for securing outer needle 8 to needle assembly 6.

Inner needle 10 has a tab 20 for allowing a rotation mechanism 18 to adjust the angular position of needle 10. Rotation mechanism 18 may rotate relative to needle assembly housing 7 and allows the user of the present invention to rotate inner needle 10 with one hand while holding handle assembly 4 with the other hand. In the preferred embodiment of the present invention, outer needle 8 is held in a fixed position relative to the rest of biopsy device 2 and inner needle 10 may be rotated about its longitudinal axis. However, it is recognized that other embodiments may allow outer needle 8 or both needles to rotate.

In the preferred embodiment, the driving mechanism comprises an electromagnet 26 and permanent magnet 24 attached to the proximate end of inner needle 10. Electromagnet 26 is secured in handle assembly 4. Handle assembly 4 includes a handle cavity 28 for housing a power source and control circuitry. In the preferred embodiment, the power source comprises a rechargeable battery that may be recharged by an inductive coil. Such a design is well known in the art. Alternatively, the power source may comprise a power cord that would be connected to an external power supply. A transformer and control circuitry may be included in cavity 28 for regulating the power from an external power source.

Figure 3:
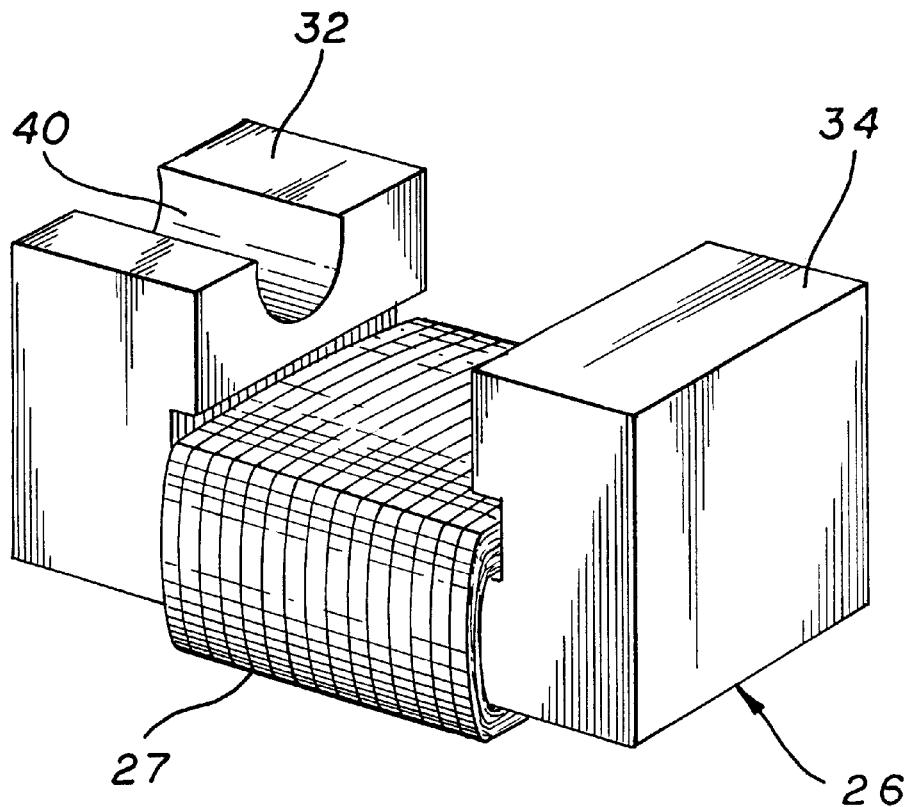
FIG. 3 is a perspective view of the electromagnet of one embodiment of the invention.
Figure 4:
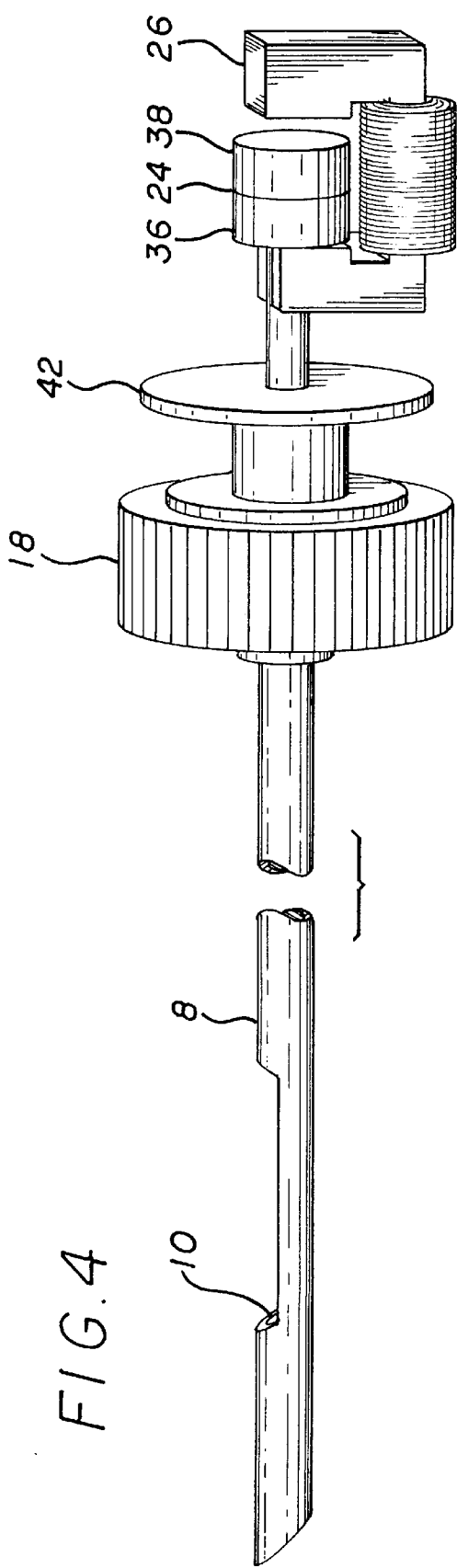
FIG. 4 is a perspective view of the driving mechanism rotation mechanism of one embodiment of the invention.

As seen in FIGS. 3 and 4, the driving mechanism of the preferred embodiment uses an oscillating electrical current to oscillate the polarity of electromagnet 26. An electrical circuit may be included for providing an oscillating current in a design that is well known in the art. The electromagnet 26 is U-shaped having opposing left and right ends 32 and 34. Groove 40 is provided for allowing inner needle 10 to extend past left end 32. Permanent magnet 24 is located in the gap between left and right ends 32 and 34. As the polarity of electromagnet 26 is oscillated, permanent magnet 24 is alternately repelled and attracted by left and right ends 32 and 34 of electromagnet 26. The resulting forces creates an oscillating motion in permanent magnet 24 which imparts and an oscillating motion on inner needle 10. The frequency of the oscillation may be predetermined to achieve the optimum cutting motion and means may be provided for adjusting the frequency to suit different kinds of tissue.

It is understood that the preferred embodiment of the driving mechanism represents only one possible configuration. Other possible driving mechanisms may include a solenoid driven by an oscillating electrical current or an electrical motor mechanically linked to the needle. Such driving mechanisms are well known in the art. Furthermore, the driving mechanism may be used to drive either inner needle 10 or outer needle 8 or both.

Also seen on FIG. 4 is a guide spacer 42 and rotation mechanism 18. Guide spacer 42 is used to guide inner needle 10 but inner needle 10 may freely rotate and move along its longitudinal axis while engaged in guide spacer 42. Guide spacer 42 also maintains inner needle 10 at its proper position within needle assembly housing 7.

Figure 6:
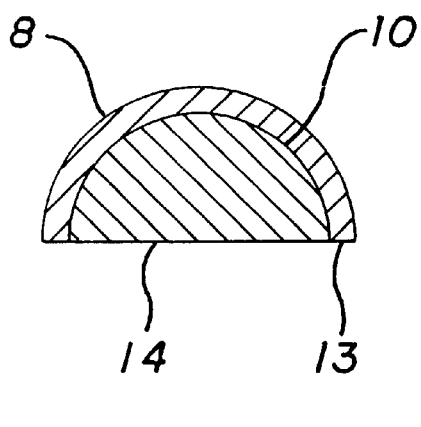
FIG. 6 is a cross sectional view of the outer needle and the inner needle in its open position along line A as seen in FIG. 1.
Figure 7:
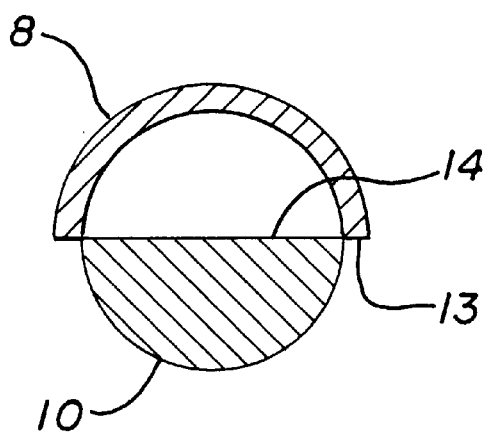
FIG. 7 is a cross sectional view of the outer needle and the inner needle in its closed position.
Figure 5:
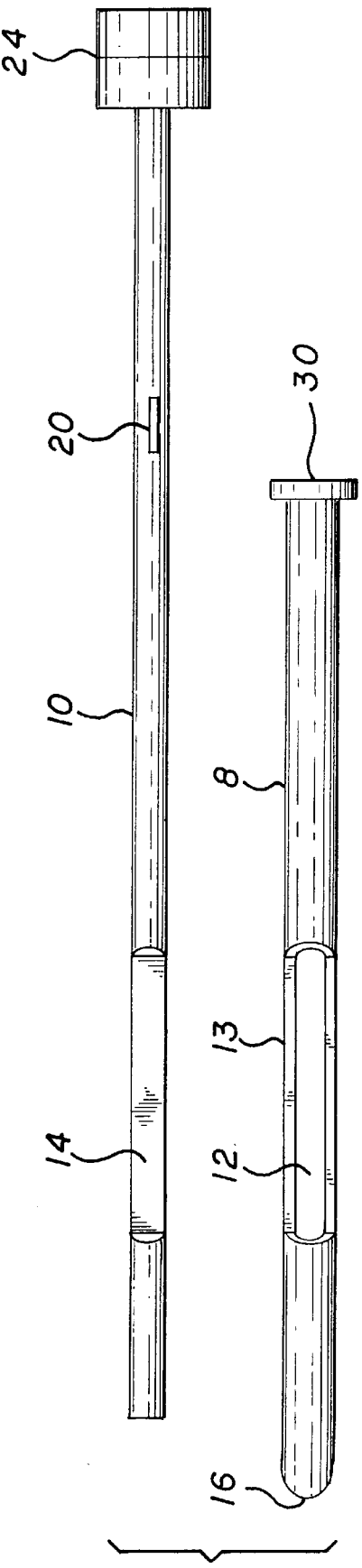
FIG. 5 is a top view of the inner and outer needle of the invention.

As seen in FIGS. 5, 6, and 7, outer needle 8 comprises an opening 12 which is aligned with a flat cutting surface 14 of inner needle 10. A cutting edge 13 defines and surrounds opening 12 and cutting edge 13 is sharp so as to easily sever tissue. As seen in FIG. 7, inner needle 14 is in its closed position when its semicircular surface, opposite to cutting surface 14, fills opening 12. In this position, an internal chamber is formed between cutting surface 14 and the inner surface of outer needle 8. This position reduces the possibility of non-target tissue catching on cutting edge 13. As seen in FIG. 6, inner needle 14 is in its open position when cutting surface 14 is fully exposed in opening 12.

The needles shown in FIG. 5 represent one possible configuration. The length and diameter of the needles and the size of opening 12 may be varied to meet the needs of the procedure.

To perform a normal biopsy procedure with the present invention, the patient is usually given a local anesthetic a few minutes before the procedure. Rotation mechanism 18 is adjusted so that inner needle 8 is in its closed position. Needle assembly 6 may have means for indicating when inner needle 8 is in its closed and open positions. Such means may comprise an arrow on needle assembly housing 7 and "closed" and "open" markers on rotation mechanism 18. The position of inner needle 8 may also be determined by direct visual inspection. Once inner needle 8 is in its closed position, the device is inserted into a patients body so that opening 12 of outer needle 8 abuts target tissue. Various means are well known in the art for locating the position of a tumor and for positioning medical instruments within a patient. Such means may also be used to position the present invention.

Once opening 12 is properly positioned, the user will rotate inner needle 10 to its open position using rotation mechanism 18. The user then activates the driving mechanism to oscillate inner needle 10 and rotates inner needle 10 towards its closed position. As cutting surface 14 rotates, tissue is pinched between cutting surface 14 and cutting edge 13. The combined effect of the oscillating motion of inner needle 10 and the pinching force, severs the tissue as inner needle 10 rotates towards its closed position. The device provides an uniform sample that is not torn from surrounding tissue. The severed tissue is captured in the cavity formed between cutting surface 14 and the inner surface of outer needle 8. Once inner needle 10 is in its closed position, the driving mechanism is deactivated and the device is withdrawn from the patients body.

During normal operation, the driving mechanism need only be active for a few seconds. This minimizes any discomfort to the patient that may be caused by vibration. The tissue sample may be removed from the device by rotating inner needle 10 to its open position. Needle assembly 6 may be separated from handle assembly 4 and discarded. Handle assembly 4 may be placed in a recharging stand for recharging the battery.

By severing tissue with a clean cutting action rather than a tearing action, the present invention produces less trauma to a patient than other biopsy devices. The wound created by the present invention will take less time to heal and the patient will experience less pain during and after the procedure. Furthermore, the sample produced is more uniform and will provide more accurate results.

It will be apparent that various modifications can be made to the biopsy device and method described above and shown in the drawings within the scope of the present invention. The size, configuration and arrangement of components can be different to meet specific requirements. Therefore, the scope of the present invention is to be limited only by the following claims:

What is claimed is:

1. A biopsy device for removing tissue from a body, comprising:

(A) a hollow outer needle, said outer needle having an opening defined by a sharp cutting edge;

(B) a inner needle received within said outer needle having a cutting surface substantially aligned with said opening of said outer needle and a substantially solid center, said inner needle having a substantially semi-circular cross-section at said cutting surface, said outer needle and said inner needle having a common longitudinal axis and being adapted to rotate and translate relative to each other;

(C) a rotation mechanism for producing relative rotation between said inner needle and said outer needle whereby the tissue protrudes into said opening and is pinched between said cutting edge and said cutting surface and severed from the body, wherein the severed tissue may be held between said inner needle and said outer needle while said inner needle and said outer needle are withdrawn from the body; and (D) a driving mechanism for oscillating either said outer needle or said inner needle or both along the longitudinal axis whereby a cutting motion is provided for severing the tissue.

2. The biopsy device of claim 1 wherein said driving mechanism comprises an electromagnet driven by an oscillating electrical current and a permanent magnet attached to either said outer needle or said inner needle or both.

3. The biopsy device of claim 1 wherein the driving mechanism comprises a solenoid driven by an oscillating electrical current.

4. The biopsy device of claim 1 wherein the driving mechanism comprises an electrical motor and linkage means for transferring power to said outer needle or said inner needle or both.

5. The biopsy device of claim 1 further comprising a battery for providing electrical power to said driving mechanism and an inductive coil for recharging said battery.

6. The biopsy device of claim 1 wherein said rotation mechanism for producing relative rotation between said inner needle and said outer needle holds said outer needle in a constant rotational position relative to the tissue and rotates said inner needle relative to said tissue.

7. A biopsy device for removing tissue from a body, comprising:
- (A) a needle assembly for severing tissue, said needle assembly comprising:
    - (a) an outer needle having an opening defined by a sharp cutting edge;
    - (b) an inner needle received within said outer needle having a cutting surface substantially aligned with said opening of said outer needle, said inner needle having a substantially solid center and a partially circular cross-section at said cutting surface, wherein the tissue may be held between said outer needle and said cutting surface of said inner needle when the tissue is severed from the body, said outer needle and said inner needle being adapted to be rotated and translated relative to each other;
    - (c) a needle assembly housing attached to said outer needle and said inner needle; and
- (B) a handle assembly for providing a handle for manipulating said biopsy device wherein said handle assembly and said needle assembly may be removably attached to each other.

8. The biopsy device of claim 7 wherein said needle assembly further comprises a rotation mechanism adapted to produce relative rotation between said inner needle and said outer needle.

9. The biopsy device of claim 7 wherein said inner and outer needles have a common longitudinal axis and said handle assembly comprises a driving mechanism adapted to oscillate said outer needle or said inner needle or both along said longitudinal axis.

10. The biopsy device of claim 9 wherein said driving mechanism comprises at least one electromagnet driven by an oscillating electrical current and a permanent magnet attached to said inner needle or said outer needle or both.

11. The biopsy device of claim 9 wherein said driving mechanism comprises at least one solenoid driven by an oscillating electrical current.

12. The biopsy device of claim 9 wherein said driving mechanism means comprises at least one electrical motor and linkage for transferring power from said electrical motor to said inner needle or said outer needle or both.

13. A method for removing tissue from a body comprising the steps of:
- (A) inserting into the body a device having an outer needle and an inner needle, said outer needle having an opening defined by a cutting edge and said inner needle being adapted to be received in said outer needle and having a cutting surface substantially aligned with said opening of said outer needle when said inner needle is operably positioned in said outer needle, said inner needle and said outer needle have a common longitudinal axis, said inner needle further having a substantially solid center and a partially circular surface at said cutting surface;
- (B) oscillating either said inner needle or said outer needle or both along said longitudinal axis;
- (C) producing relative rotation between said inner needle and said outer needle whereby the tissue is pinched between said cutting edge and said cutting surface and severed from the body;
- (D) rotating said outer needle or said inner needle to a position where said partially circular surface fills said opening wherein severed tissue is held between said cutting surface of said inner needle and said outer needle; and
- (E) withdrawing said device from the body.

14. The method of claim 13 wherein said inner needle has a semicircular surface corresponding to said cutting surface and further comprising the step of rotating said outer needle or said inner needle to a position where said semicircular surface fills said opening before said device is inserted into the body whereby tissue is less likely to be severed as said device is inserted.

* * * * *